United States Patent [19]

Cumming et al.

[11] Patent Number: 4,765,329

[45] Date of Patent: Aug. 23, 1988

[54] INTRAOCULAR LENS INSERTION INSTRUMENT

[75] Inventors: J. Stuart Cumming, Anaheim; Robert F. Redwitz, Costa Mesa, both of Calif.

[73] Assignee: Cumming, Redwitz & Wilson, Inc., Costa Mesa, Calif.

[21] Appl. No.: 109,904

[22] Filed: Oct. 19, 1987

[51] Int. Cl.$^4$ .......................... A61B 17/00; A61F 2/16
[52] U.S. Cl. ...................................... 128/303 R; 623/6
[58] Field of Search ........................ 623/6; 128/303 R

[56] References Cited

U.S. PATENT DOCUMENTS

| | | | |
|---|---|---|---|
| 4,573,998 | 3/1986 | Mazzocco | 623/6 |
| 4,585,457 | 4/1986 | Kalb | 623/6 |
| 4,600,004 | 7/1986 | Lopez et al. | 623/6 X |
| 4,681,102 | 7/1987 | Bartell | 128/303 R |

*Primary Examiner*—Ronald L. Frinks
*Attorney, Agent, or Firm*—Keith D. Beecher

[57] ABSTRACT

An intraocular lens insertion instrument for the implantation of intraocular lenses into the human eyes. The instrument is particularly intended for use in conjunction with the insertion of deformable intraocular lenses through extremely small incisions. The instrument comprises an insertion tube with a tip of reduced diameter which is inserted into the eye through a small incision; and a probe which is inserted into the tube to force an intraocular lens contained in the tube through the tip of the tube and into the eye. The handle of the probe is shaped so that its linear movement into the tube is stopped at a predetermined linear position of the probe in the tube, so as to limit the displacement of the probe into the tip of the tube. In addition, the probe may be spring-loaded into the handle to limit the force that may be applied to the lens during the insertion procedure.

5 Claims, 2 Drawing Sheets

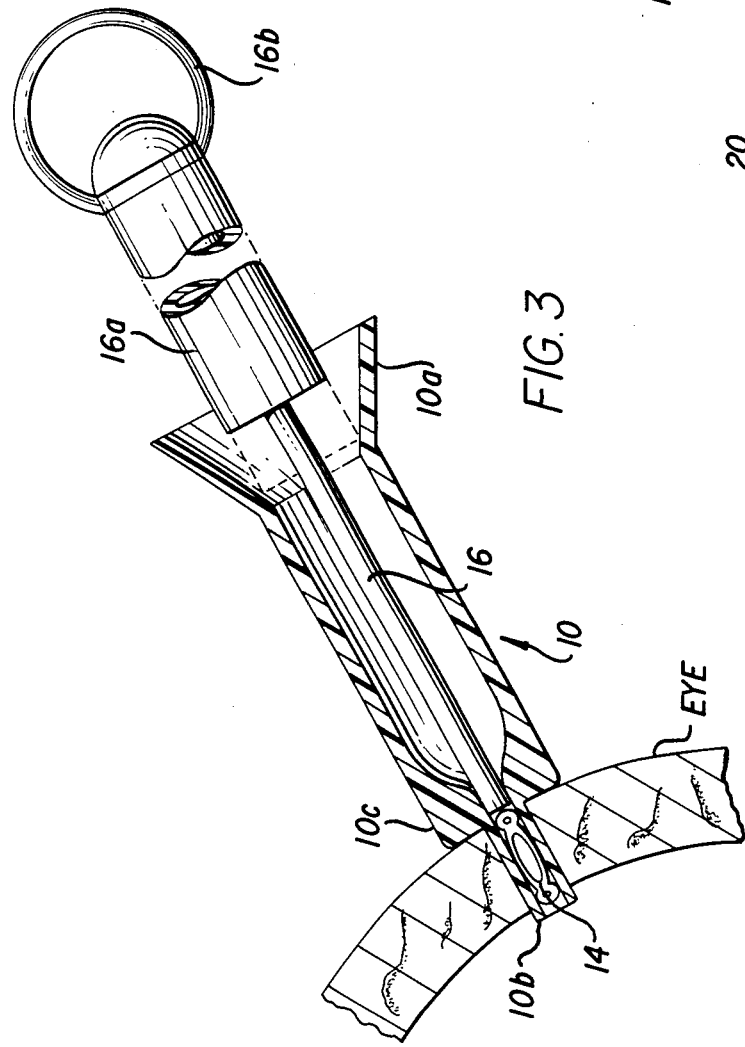
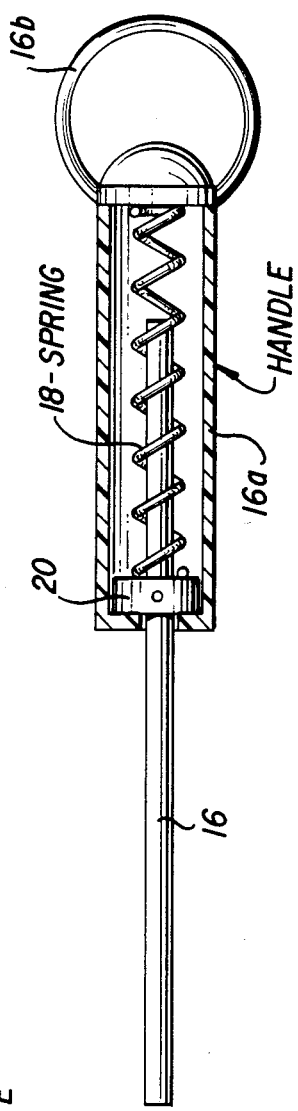

INTRAOCULAR LENS INSERTION INSTRUMENT

BACKGROUND OF THE INVENTION

The usual prior art intraocular lens is rigid, and it is formed, for example, of an appropriate transparent plastic such as methylmethacrylate. U.S. Pat. No. 4,573,998 discloses an intraocular lens which comprises a deformable optical zone with prescribed memory characteristics. The optical zone of the lens disclosed in the Patent may be deformed by rolling or folding the lens to a reduced diameter so that it may be inserted into the eye through a relatively small incision. A deformable intraocular Fresnel lens is disclosed in copending application Ser. No. 46,694 filed May 7, 1987 in the names of the present inventors.

Prior to the introduction of foldable intraocular lenses, such as those disclosed in the aforementioned patent and patent application, there was little need for insertion instruments. With the hard intraocular lenses, conventional surgical procedures and available surgical tools were sufficient for inserting the lenses. However, the advent of the soft foldable lens, coupled with the desire for small incision surgery, created a need for special insertion instruments, by which the lenses could be inserted through the relatively small incisions.

Copending application Ser. No. 5,105 filed Jan. 20, 1987 in the name of Stephen G. Hauser discloses and claims an improved instrument for folding or otherwise deforming deformable intraocular lens for convenient insertion of the lens into the eye through a small incision. The present invention, likewise, is concerned with an insertion instrument for such a purpose.

The insertion instrument of the present invention provides a convenient means for changing the cross-sectional area of a deformable intraocular lens so that the lens will pass through a relatively small incision. The instrument is capable of changing the cross-sectional area of the lens sufficiently so that it will pass through a relatively small incision, without moving into the eye with excessive force, or at excessive speed, after the lens has passed into the eye through the incision. Accordingly, the instrument of the invention prevents a permanent change in the shape of the lens after it has passed into the eye through the incision, and it also prevents damage to the lens and to the eye of the patient after it has entered the eye.

A feature of the insertion instrument of the invention is that it allows a trained nurse to place the lens in the instrument up to the point where the instrument is placed in the eye of the patient. This permits the surgeon to concentrate on the removal of the existing lens. The nurse then hands the instrument to the surgeon ready for the implantation of the new lens into the eye of the patient. This has the obvious advantage in that it relieves the surgeon from performing relatively trivial operations.

The insertion instrument of the invention is also constructed to provide the surgeon with an automatic overload protection so as to avoid the creation of potentially dangerous and hazardous conditions in the patient's eye. This is most important because, to avoid damage and injury to the patient, it may be shown that as the size of the incision decreases a corresponding reduction in force must be made for safety reasons as the lens leaves the incision and enters the eye. Accordingly, the feature of the instrument of the present invention which provides an automatic means for limiting the force that may be applied to the lens as it is inserted through the incision is most important.

The intraocular lens insertion instrument to be described herein, as mentioned above, is particularly suitable for inserting a foldable lens through a small size incision into the eye. The ultimate placement of the lens within the eye, whether anterior or posterior, is of less importance since once the lens has passed through the sclera its ultimate placement depends upon the skill of the surgeon.

It will become apparent as the description proceeds, that the instrument of the invention may also be used for the insertion of lenses designed to provide a refractive correction for other than cataract patients, that is, for refractive surgery patients.

The shape of the interior of the insertion tube is critical to reducing the insertion force required. Emperical research has demonstrated that the transition in the insertion tube from one diameter to another diameter, even though well lubricated must be not only smooth but very gradual. Any abrupt changes in this area manifest themselves in increased insertion forces and possible damage to the lens, that is, separated haptic, torn optical area, and the like.

The probe associated with the force limiting insertion probe must be stiff enough to transmit the insertion force without bending excessively. Yet it must be soft enough to preclude damaging a relatively soft lens. The best results have been obtained from a composite construction. Such a construction may consist of a hard steel core encased in a soft plastic sheath.

SUMMARY OF THE INVENTION

The intraocular lens insertion instrument of the invention in the embodiment to be described consists of two parts, comprising an insertion tube, and a force-limiting insertion probe. It is intended that all of the components of the assembly will be furnished to the surgeon in a sterilized, pre-packaged condition. The instrument is intended to be disposable.

Accordingly, an objective of the present invention is to provide a simple, inexpensive disposable instrument for inserting deformable intraocular lenses, and other deformable lenses into the human eye, which is sufficiently inexpensive in its construction to be disposable, and which is easy to use.

BRIEF DESCRIPTION OF THE DRAWINGS

FIG. 3 is a section of the insertion tube of FIG. 2, with an intraocular lens being positioned within the tube, and with a force-limiting insertion probe also being introduced into the tube; and FIG. 4 is a view of the probe of FIG. 3, with the handle being shown in section to reveal the internal operating components.

DETAILED DESCRIPTION OF THE ILLUSTRATED EMBODIMENT

Figure 1:
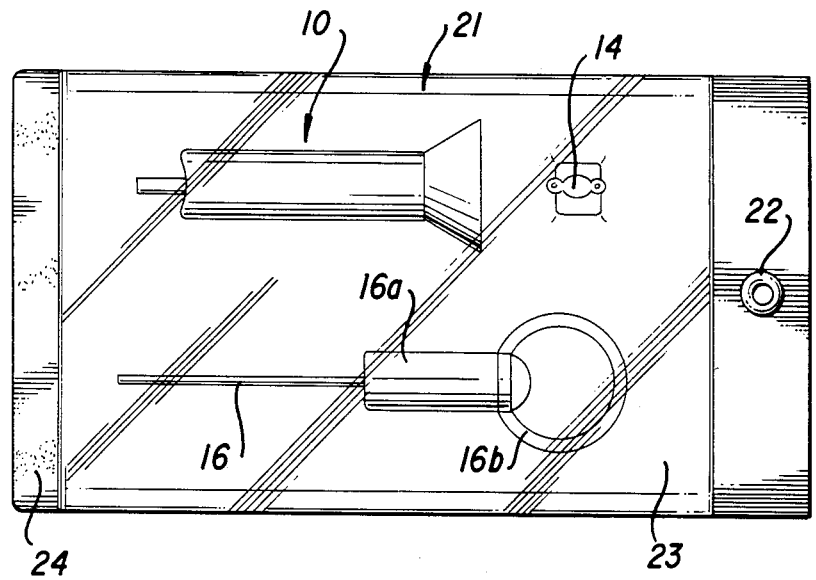
FIG. 1 is a plan view showing the components of the insertion instrument assembly of the invention in an appropriate sterile package.

As shown in FIG. 1, the insertion instrument assembly may be delivered to the surgeon pre-sterilized in a package 20 with a transparent plastic cover 21. The package has a hanger grommet 22 at one end, and a peelable opening 24 at the other end. The package may include illustrated instructions on its rear side.

Figure 2:
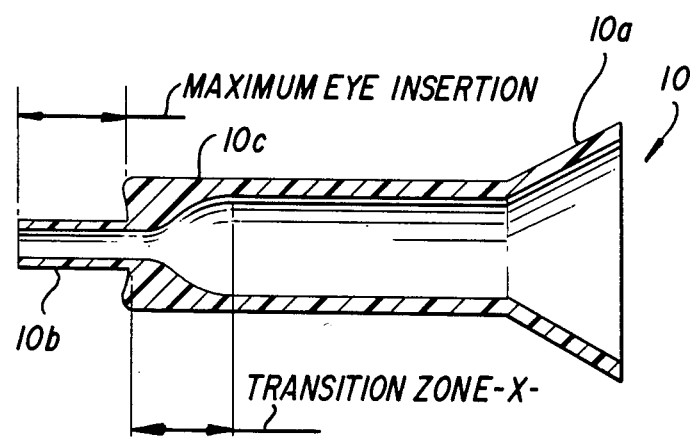
FIG. 2, is an enlarged sectional representation of one of the components of the insertion instrument assembly of the invention, namely the insertion tube.

The insertion instrument assembly of the invention as shown in FIG. 1 includes, for example, a tube 10 which is shown on an enlarged scale in FIG. 2. The tube 10 is provided with a flared end 10a, and also with an end 10b of reduced diameter, so that the end 10b defines a shoulder with the central portion 10c of the tube. The length of the end 10b determines the maximum distance the tube may be inserted through an incision into the eye of a patient. The interior of the tube is shaped to define a transition zone X which provides a gradual and smooth transition from a larger to a smaller diameter in the tube.

In the practice of the invention, a small initial incision is made by the surgeon in a selected position in the eye, by instruments normally used for that purpose. As shown in FIG. 3, the end 10b of the tube 10 is inserted through a small incision into the eye of a patient.

After coating a deformable intraocular lens 14 (FIG. 3) with the lubricant, the lens is placed into the tube with a configuration folded lengthwise in half, as shown in FIG. 3, with the long axis of the folded lens being parallel to the tube. Then an insertion probe 16 is introduced into the tube 10 through the flared end 10a, until the tip of the probe engages the end of the lens, as shown in FIG. 3. The probe is then pushed against the flared end 10a of the tube, thereby pushing the lens 14 through the transition zone X and through end 10b of the tube into the eye. The transition zone X (FIG. 2) serves to fold the lens 14 into a very small diameter to allow its insertion into the eye through a very small incision.

The probe 10 includes a handle 16a of a diameter such that the handle cannot enter into the tube 10, so that the end of the handle serves as a means for limiting the displacement of the probe into the tube. A thumb loop 10b may also be provided.

As shown in FIG. 4, the handle 16a of the probe 16 includes a spring 18 which engages a bushing 20 secured to the probe 16. The spring 18 serves as a force limiting means, so as to limit the force that may be applied by the probe to the lens 14.

Accordingly, no particular skill is required on the part of the surgeon for inserting lenses by the use of the insertion instrument of the invention. This is because the insertion instrument itself assures that the probe will not move into the eye of the patient, and the construction of the probe insures that the insertion force exerted against the lens 14 will not exceed a predetermined safe maximum. To further reduce the possibility of damage to the lens itself, the end of the probe 16 is made of a soft plastic. The probe itself may be entirely encased in a soft plastic resulting in a multi-piece construction.

The invention provides, therefore, a simple and inexpensive insertion instrument which is particularly useful for the implantation of a deformable intraocular lens into the eye of a patient, with the instrument being constructed so that the lens may easily be deformed into the desired configuration for insertion into the eye through a relatively small incision, and with the instrument being further constructed so that the force exerted on the lens during the implantation procedure is held below a predetermined safe threshold, and the instrument is also constructed so that the probe component cannot be inserted into the eye with resulting damage to the eye.

The invention provides, therefore, an insertion instrument for deformable intraocular lenses which is both safe and effective, and which is particularly useful for the insertion of flexible intraocular lenses through relatively small incisions. The instrument is constructed so that the insertion distance is limited to a safe limit. The instrument itself requires a minimum of manual dexterity, and enables intraocular lenses to be inserted into the eye quickly and effectively, for example, in less than one minute.

The insertion instrument of the invention is also advantageous in that it enables the lens to be inserted through the incision into the eye under a controlled force and pressure and without any tendency to cause permanent damage to the lens or to the eye. Moreover, the insertion instrument is capable of handling a wide variety of lenses, including the lenses disclosed in copending application Ser. No. 46,694 referred to above, in all diopter ratings, with equal ease. A feature of the instrument is that it is sufficiently inexpensive so as to be disposable after a single use. Also, the instrument is constructed so that it may be factory sterilized and stored for reasonable periods of time in package 20 (FIG. 1) to be opened only when the instrument is needed.

It will be appreciated that while a particular embodiment of the invention has been shown and described, modifications may be made. It is intended in the claims to cover all modifications which come within the true spirit and scope of the invention.

We claim:

1. An instrument for inserting a lens through an incision into the eye of a patient, comprising: a tubular member having a central section of a particular diameter and a first end section of a reduced outer diameter with respect to said central section to be received in the incision, said first end section forming a shoulder with said central section to limit the distance that the first end section may be inserted into the incision, an elongated probe received into said tubular member through a second end section thereof, a handle mounted at one end of said probe, said handle having a diameter greater than the inner diameter of said central section of said tubular member to prevent the handle from entering said central section and thereby limiting the linear displacement of said probe into said tubular member, said probe being linearly movable in said handle, and a spring mounted in said handle and coupled to said probe to provide a spring-bias action to said probe so as to limit the maximum force that may be exerted on said probe by said handle as said probe is inserted into said tubular member.

2. The instrument defined in claim 1, in which the inner diameter of said first end section is reduced with respect to the inner diameter of said central section, and the inner diameter of said central section at the end thereof adjacent to said first end section is curved inwardly towards said first end section to provide a transition zone to permit a folded flexible lens to be folded and inserted into said first end section through said central section and held in a folded configuration in said first end section.

3. The instrument defined in claim 1, in which the second end section of said tubular member is flared outwardly.

4. The instrument defined in claim 2, in which said transition has a gradual curvature to reduce insertion forces and virtually to eliminate damage to soft intraocular lenses.

5. The instrument defined in claim 1, in which the probe is constructed of composite materials to achieve maximum stiffness while presenting a soft surface to preclude damage to the lens being inserted.

* * * * *